(12) United States Patent
Sternberg (10) Patent No.: US 8,562,876 B2
(45) Date of Patent: Oct. 22, 2013

(54) MULTIZONE POLYMER MEMBRANE AND DIALYZER

(75) Inventor: Shmuel Sternberg, Palatine, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 865 days.

(21) Appl. No.: 11/948,754

(22) Filed: Nov. 30, 2007

(65) Prior Publication Data

US 2009/0139925 A1    Jun. 4, 2009

(51) Int. Cl.
*B01D 67/00*    (2006.01)
*B29C 44/04*    (2006.01)

(52) U.S. Cl.
USPC ........ 264/48; 210/321.72; 210/486; 210/490; 210/645; 210/651; 427/243; 427/244; 428/195.1; 428/36.5; 428/212

(58) Field of Classification Search
USPC ............. 428/212; 210/490, 321.84, 645, 651, 210/321.8
See application file for complete search history.

(56) References Cited

U.S. PATENT DOCUMENTS

| | | | |
|---|---|---|---|
| 3,133,132 A | 5/1964 | Loeb et al. | |
| 3,344,214 A | 9/1967 | Manjikan et al. | |
| 3,417,870 A | 12/1968 | Bray | |
| 3,546,209 A | 12/1970 | Lipps, Jr. | |
| 4,039,440 A | 8/1977 | Cadotte | |
| 4,125,468 A * | 11/1978 | Joh et al. | 210/321.8 |
| 4,137,113 A | 1/1979 | Kanamaru et al. | |
| 4,173,537 A | 11/1979 | Newhart | |
| 4,239,714 A | 12/1980 | Sparks et al. | |
| 4,276,173 A | 6/1981 | Kell et al. | |
| 4,333,906 A | 6/1982 | Porter et al. | |
| 4,385,094 A | 5/1983 | Tanaka et al. | |
| 4,430,278 A | 2/1984 | Jones, Sr. | |
| 4,527,999 A | 7/1985 | Lee | |
| 4,777,073 A | 10/1988 | Sheth | |
| 4,824,568 A | 4/1989 | Allegrezza, Jr. et al. | |
| 4,842,736 A | 6/1989 | Bray et al. | |
| 4,906,375 A | 3/1990 | Heilmann | |
| 4,919,860 A | 4/1990 | Schindler et al. | |

(Continued)

FOREIGN PATENT DOCUMENTS

| | | |
|---|---|---|
| GB | 2230205 | 7/1985 |
| WO | 2005002712 | 1/2005 |
| WO | 2005047857 | 5/2005 |

OTHER PUBLICATIONS

Effect of dialyser membrane pore size on plasma homocysteine levels in haemodialysis patients; Nephrology Dialysis Transplantation; XP-002512201; Nephrol Dial Transplant (2003) 18: 2596-2600; De Vriese, Langlois, Bernard, Geerolf, Stevens, Boelaert, Schurgers, Matthys.

(Continued)

*Primary Examiner* — Dirk Bass
(74) *Attorney, Agent, or Firm* — K&L Gates LLP (57) ABSTRACT

Membranes are made from polymers and heat treated so that they have at least two zones with pores of different sizes. Pores with a smaller size have a lower molecular weight cut off than pores with a larger size. Zones with pores of different sizes may also be made by coating portions of membranes with polymer coatings. Membranes with pores of different sizes may be used in dialyzers for hemofiltration, hemodiafiltration, and other hemodialysis procedures. The membranes may also be used in other separation processes.

17 Claims, 5 Drawing Sheets

(56) References Cited

U.S. PATENT DOCUMENTS

| | | | |
|---|---|---|---|
| 4,933,084 | A | 6/1990 | Bandel et al. |
| 4,980,063 | A | 12/1990 | Mahoney et al. |
| 5,013,339 | A | 5/1991 | Mahoney et al. |
| 5,017,292 | A | 5/1991 | DiLeo et al. |
| 5,049,282 | A * | 9/1991 | Linder et al. ............... 210/651 |
| 5,096,637 | A | 3/1992 | DiLeo et al. |
| 5,120,594 | A | 6/1992 | Mrozinski |
| 5,151,082 | A | 9/1992 | Gorsuch et al. |
| 5,228,994 | A | 7/1993 | Tkacik et al. |
| 5,298,165 | A * | 3/1994 | Oka et al. ............... 210/645 |
| 5,538,642 | A | 7/1996 | Solie |
| 5,641,405 | A | 6/1997 | Keshaviah et al. |
| 5,656,372 | A | 8/1997 | Gentile et al. |
| 6,773,591 | B2 | 8/2004 | Boivin et al. |
| 7,087,168 | B2 | 8/2006 | Oishi et al. |
| 7,208,200 | B2 | 4/2007 | Kools |
| 2003/0201560 | A1 | 10/2003 | Vollrath et al. |
| 2003/0209485 | A1 | 11/2003 | Kools |
| 2005/0170159 | A1* | 8/2005 | Ramsey et al. ............... 428/212 |
| 2006/0144782 | A1* | 7/2006 | Buck ............... 210/500.23 |

OTHER PUBLICATIONS

Effect of dialyser membrane pore size on plasma homocysteine levels in haemodialysis patients; An S. De Vriese, Michel Langlois, Dirk Bernard, Inge Geerolf, Lut Stevens, Johan R. Boelhart, Mario Schurgers, Erve Matthys, *Nephrology Dialysis Transplantation* (2003) 18:2596-2600.

Characterization of polyethersulfone hemodialysis membrane by ultrafiltration and atomic force microscopy; Abstract; Jalal Barzin, C. Feng, K. C. Khulbe, T. Matsurra, S. S. Madaeni, H. Mirzadeh, *Journal of Membrane Science*, vol. 237, Issues 1-2, Jul. 1, 2004, pp. 77-85.

Comprehensive two-dimensional separation based on coupling micellar electrokinetic chromatography with capillary isoelectric focusing; Li Sheng and Janusz Pawliszyn; Department of Chemistry, University of Waterloo, Waterloo ON, Canada, *Analyst*, 2002; vol. 127, pp. 1159-1163; The Royal Society of Chemistry.

Written Opinion of the International Searching Authority—PCT/US2008/078889 mailed Feb. 5, 2009, 9 pages.

* cited by examiner

MULTIZONE POLYMER MEMBRANE AND DIALYZER

BACKGROUND

The present invention relates generally to separation processes and medical treatments. More specifically, the present invention relates to separation membranes and to medical fluid treatments using such membranes, such as treatment of renal failure and fluid removal from persons whose kidneys do not function well.

Hemodialysis in general uses diffusion to remove waste products from a patient's blood. A diffusive gradient that occurs across the semi-permeable dialyzer between the blood and an electrolyte solution called dialysate causes diffusion. Hemofiltration is an alternative renal replacement therapy that relies on a pressure difference and thus a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the hemofiltration treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration is a treatment technique that combines convective and diffusive clearances. Hemodiafiltration uses dialysate to flow through a dialyzer, similar to standard hemodialysis, providing diffusive clearance. In addition, substitution solution is provided directly to the extracorporeal circuit, providing convective clearance.

Home hemodialysis has declined in the last twenty years because costs have increased, but reimbursement or insurance coverage has not increased, even though the clinical outcomes of this technique are more attractive than conventional hemodialysis. One of the drawbacks of home hemodialysis is the need for a dedicated water treatment, which includes equipment, water connection and drainage. Installing and using those components is a difficult and cumbersome task that can require a patient's home to be modified. Nevertheless, there are benefits to daily hemodialysis treatments versus bi- or tri-weekly visits to a treatment center.

In particular, a patient receiving more frequent treatments removes more toxins and waste products than a patient receiving less frequent but perhaps longer treatments, leading to a healthier, more energetic person. What is needed is a better way to rid a patient's blood of small and even mid-size molecules, a better way that could involve a combination of known and reliable convective and diffusive transport of the small and medium molecules through the dialysis membranes.

SUMMARY

Embodiments of the invention provide a hollow fiber filter, very useful for separation processes, such as dialysis processes, including hemodialysis and home hemodialysis. The fibers have pores of different sizes in two different portions of the fiber, such as a larger pore size in one portion and a smaller pore size in another portion. This size difference allows different molecules or species of different sizes to have different permeation rates through the two different portions. Embodiments of the invention need not be long hollow fibers, but may also be in the form of sheet membranes, such as squares or rectangles. Sheet membrane filters having areas with at least two pores sizes may be just as useful as hollow fiber filters. Such sheet membrane filters may also be wound into a spiral shape to make a spiral-wound separator. Of course, the spiral-wound separator will also include additional components, such as spacers or separators, just as other separators made from sheet membranes or hollow fiber membranes may also have additional components.

One embodiment is a method for making a permeable membrane. The method includes steps of forming a membrane, the membrane including a polymer continuum with a first plurality of pores, and immersing a first portion of the membrane that is less than the entire membrane in a first environment, wherein the membrane forms a second plurality of pores in the portion of the membrane subjected to the first environment, a size of the second plurality of pores smaller than a size of the first plurality of pores.

Another embodiment is a method of making a permeable polymer membrane for hemodialysis. The method includes steps of forming a polymer membrane for hemodialysis, the polymer membrane including a first plurality of pores, subjecting a first portion of the polymer membrane, the first portion less than the entire polymer membrane, to an environment at a first temperature, wherein the first temperature is higher than a temperature of formation of the membrane, wherein the membrane forms a second plurality of pores in the first portion at the first temperature, a size of the pores of the second plurality smaller than a size of the pores of the first plurality.

Another embodiment is a method of making a permeable membrane. The method includes steps of forming a polymer membrane, the polymer membrane comprising a first plurality of pores, and coating a first longitudinally-spaced portion of the polymer membrane, the first portion less than the entire membrane, wherein the coating forms a second plurality of pores in the first portion, a size of the pores of the second plurality smaller than a size of the pores of the first plurality, the coating reducing the size of the pores in the first portion.

Another embodiment is a multizone polymer membrane. The multizone polymer membrane includes a first zone having a first plurality of pores of a first size and a second zone having a second plurality of pores of a second size, the second size less than the first size.

Another embodiment is a multizone polymer membrane for hemodialysis. The multizone polymer membrane for hemodialysis includes a first zone having a first plurality of pores of a first size, the first plurality formed at a first temperature, and a second zone having a second plurality of pores of a second size, the second size smaller than the first size, the second plurality formed at a second temperature greater than the first temperature, wherein the membrane and the first and second pluralities are suitable for hemodialysis.

Another embodiment is a multi-zone polymer membrane. The multi-zone polymer membrane includes a longitudinally-spaced first zone and a second zone, the first zone including a first plurality of pores of a first size, and a second zone including a second plurality of pores of a second size, the second size less than the first size, the second zone including a coating not on the first zone, the coating effectively reducing the size of the pores of the second zone.

Additional features and advantages are described herein, and will be apparent from, the following Detailed Description and the figures.

DETAILED DESCRIPTION

Early techniques for producing semipermeable membranes for separation processes used casting techniques on discrete molds or plates, as described in U.S. Pat. Nos. 3,133,132 and 3,344,214. Hollow fiber membranes for separation are now typically made by more-efficient techniques that use a spinning process to produce a hollow fiber with a generally tubular shape. For example, the Lipps process for cellulosic hollow fibers from cellulose diacetate and a plasticizer is disclosed in U.S. Pat. No. 3,546,209. In another example, U.S. Pat. No. 4,276,173 discloses melt spinning mixtures of cellulose acetate, glycerine, and polyethylene glycol (PEG) to form hollow capillary fibers. After cooling, typically to 0° C., water is used to leach out the glycerine and polyethylene glycol. Each of these referenced patents is hereby incorporated by reference in its entirety. The cuproammonium process, as described in U.S. Pat. No. 4,933,084, which is hereby incorporated by reference in its entirety, is well known and yields hollow dialysis fibers in a variety of cross-sectional shapes, including circular, elliptical, rounded polygons such as rounded triangles and squares, kidney shapes, and other shapes. Dimensions for the finished fibers included wall thicknesses of about 10-20 microns, inner diameters (short axis) from 150 to 200 microns, and long axis from 250 microns to 350 microns. One example is an elliptical shape with a wall thickness of about 17 microns and inner dimensions, for the long and short axes, respectively, of 290 and 160 microns. All of these membranes are unitary, i.e., they are seamless or made as a continuum, that is, a continuous tube of polymer formed by a spinning process in which a polymer casting or other solution or mixture is pumped through one or more nozzles with air or other gas in the center to prevent collapse of the tube. The membranes may also be made by any other suitable process for forming a unitary membrane or continuum.

Hollow fiber membranes are not limited to cellulosics, and wet spinning processes may be used to form hollow fiber membranes from many other compositions. As disclosed in U.S. Pat. No. 5,656,372, which is hereby incorporated by reference in its entirety, other suitable materials include thermoplastic polymers, thermosetting polymers, gels, and hydrogels. Specific materials that may be used, besides cellulosics, include acrylic copolymers, polyvinylidene fluoride, polyurethane isocyanates, alginates, polysulfones, polyvinyl alcohols, polyacrylonitriles, and mixtures thereof. While the membrane forming material may be a melt, it is preferably a solution. Suitable solvents for use in forming the solution include water soluble organic solvents such as dimethylacetamide, dimethylformamide, acetone, dimethylsulfoxide, N-methylpyrolidone, acetonitrile, and mixtures thereof, as well as other solvents such as hexane, diethylether, methylene chloride, and mixtures thereof.

Properties of the membranes desirably include a high rate of transfer or permeability, as well as selectivity to what passes through the membrane. The selectivity is sometimes expressed as molecular weight cut-off (MWCO), that is, the molecular weight or size of the molecules which the membrane will allow to pass through. A membrane with a high MWCO will have larger pores and will be less selective, allowing larger molecules to pass through. For example, it is desired to allow most molecules of beta-2-microglobulin (MW about 11,600 to 11,800 Da) to pass, while allowing almost no passing of serum albumin (MW about 66,400 Da) from the patient's blood through the membrane and into the dialysate. A membrane with a lower MWCO has smaller pores and is more selective, or selectively permeable, allowing only smaller molecules, molecules with a lower molecular weight, to pass through. The membranes or hollow fibers discussed herein are semi-permeable, because their pore sizes allow only molecules or species of certain sizes or shapes to pass through. However, such membranes are more easily referred to as permeable, rather than semi-permeable, in contrast with solid substances, such as a solid metallic sheet, though which nothing can permeate. Thus, as used herein, permeable or semi-permeable membranes allow selected species or molecules to pass through, depending on the particular pore size and particular species or molecule attempting passage.

One example of cellulose acetate fibers with varying pore size is found in the literature, *Effect of Dialyzer Membrane Pore Size on Plasma Homocysteine Levels in Haemodialysis Patients*, An S. De Vriese et al., Nephrol. Dial. Transplant., vol. 18, pp. 2596-2600 (2003), and which is hereby incorporated by reference in its entirety. This article discloses three different commercially-available acetate fibers, all of which had an inner diameter of about 200 micrometers and wall thickness of about 15 micrometers. The three fibers had pore sizes of 5.0 nm, 7.0 nm, and 7.8 nm, and respectively, a ratio of open pores of 63, 70 and 84 percent. The sieving coefficients for beta-2-microglobulin were 0.36, 0.88 and unity, respectively. The ultrafiltration coefficient for the three were, respectively, 12.8, 29.8, and 66.9 ml/h/mm Hg. These data demonstrate the appropriate range of pore sizes and also demonstrate that pore size affects elimination of toxins from the blood, including beta-2-microglobulin. In addition, the membranes with the largest pores were effective in reducing plasma homocysteine levels in the blood, while not passing excessive amounts of serum albumin. Elevated levels of plasma homocysteine in the blood may be a factor in cardiovascular disease, including high blood pressure and heart attacks. It is clearly desirable that a dialysis membrane include at least some pores of larger size at least for the purpose of reducing homocysteine in the blood.

Polyvinylpyrrolidone (PVP) may also be used in making polyethersulfone (PES) hollow fiber membranes. PES is sometimes incorrectly abbreviated as "polysulfone." Suitable membranes may also be made from polyarylethersulfone. One study found that excellent hollow fiber membranes were prepared from solutions of PES/PVP (18 parts to 3 parts or 18 parts to 6 parts, respectively, by weight), in N,N-dimethylacetamide. See *Characterization of Polyethersulfone Hemodialysis Membrane by Ultrafiltration and Atomic Force Microscopy*, by Jalal Barzin et al., J. Membrane Science, v. 237, issues 1-2, 1 Jul. 2004, pp. 77-85, which is hereby incorporated by reference in its entirety. After the fibers were created by spinning, they were treated either in either hot water at 95° C. for 30 minutes or air for 150° C. for 5 minutes. The untreated fibers had pore diameters from about 12-16 nm. Fibers treated in water at 95° C. for 30 minutes had pore sizes from about 15-19 nm. This increase probably is accounted for by simply eliminating solvent and completing polymerization. A different set of membranes was heated in air at 150° C. for 5 minutes, and were determined to have pores with diameters from 3.1-3.8 nm, indicating a much lower MWCO.

Polyvinylidenefluoride (PVDF) fibers may also be prepared by processes of spinning and treatment, as disclosed in U.S. Pat. No. 5,013,339, which is hereby incorporated by reference in its entirety. The fibers are prepared by spinning a mixture of PVDF polymer, glycerol acetate or acetates, and optionally, glycerol. The glycerol acetate may be the monoacetate, the diacetate, triacetate, or mixtures thereof. Membrane fibers suitable for dialysis were prepared. After the fibers were spun, they were quenched or coagulated in a liquid, such as water, one or more of the glycerol acetates, or glycerol, at a constant temperature for less than about 30 seconds. The membranes are then dried. The wall thickness ranged from 10 to 30 microns, with an outer diameter from about 175 to 300 microns.

One way to modify the pore size and thus the MWCO is to add pore blockers during processing. As noted in U.S. Pat. No. 4,239,714, which is hereby incorporated by reference in its entirety, this technique adds pore blocking agents of particular molecular weights, such as proteins and enzymes. The process involves making a porous membrane and filling the pores with a volatile liquid such as alcohols, esters, ketones, and aromatics. The volatile liquid is then partially evaporated to form voids at the entrances to the pores. A concentrated solution of the pore-blocking material is then applied to the pores. The pore-blocking material is insoluble in the volatile liquid and is configured to yield pores of the desired size. The excess pore-blocking agent is then removed and the remainder locked into position by curing, cross-linking, or other technique. This technique is clearly very expensive and tedious. Other processes also attempt to influence pore size by using solvents, such as U.S. Pat. Nos. 4,430,278 and 5,120,594. Each of these patents is hereby incorporated by reference in its entirety.

As noted above, hollow fiber membranes for dialysis are typically spun at one temperature, formed, and then coagulated and dried. Embodiments of the present invention use variations in temperature as a way to induce MWCO in different zones in a final stage of manufacture. For example, a fiber may be made by any of the methods described above, ending by immersion in a bath of ice water at 0° C. As noted above, this will yield a membrane with a certain outer diameter, inner diameter, and pore size. The fiber is then partially immersed in a heated bath, such as a bath heated to 60° C. or 95° C., or other suitable temperature. For example, cellulose acetate fibers that are made according to U.S. Pat. No. 3,133,132 or U.S. Pat. No. 3,344,214, and treated at about 77-83° C., are able to retain salt. Without being bound to any particular theory, it is believed that the additional heat treatment consolidates the polymer and causes the pores or open areas to consolidate and shrink. Thus, a membrane formed at a first, colder temperature will have a higher MWCO and will allow larger molecules to pass through its larger pores. A portion of the membrane treated at a higher temperature will then have smaller pores and a lower MWCO. It should also be noted that both zones of the heated bath should be exposed to a temperature above the contemplated use temperature of the membrane, such as the use of body temperature, 37° C., for hemodialysis. If not, the membrane will then be exposed to this higher temperature during use, and consolidating will then occur while the membrane is in use, that is, all the pores would then shrink or consolidate to the pore size commensurate with that particular temperature.

Figure 1:
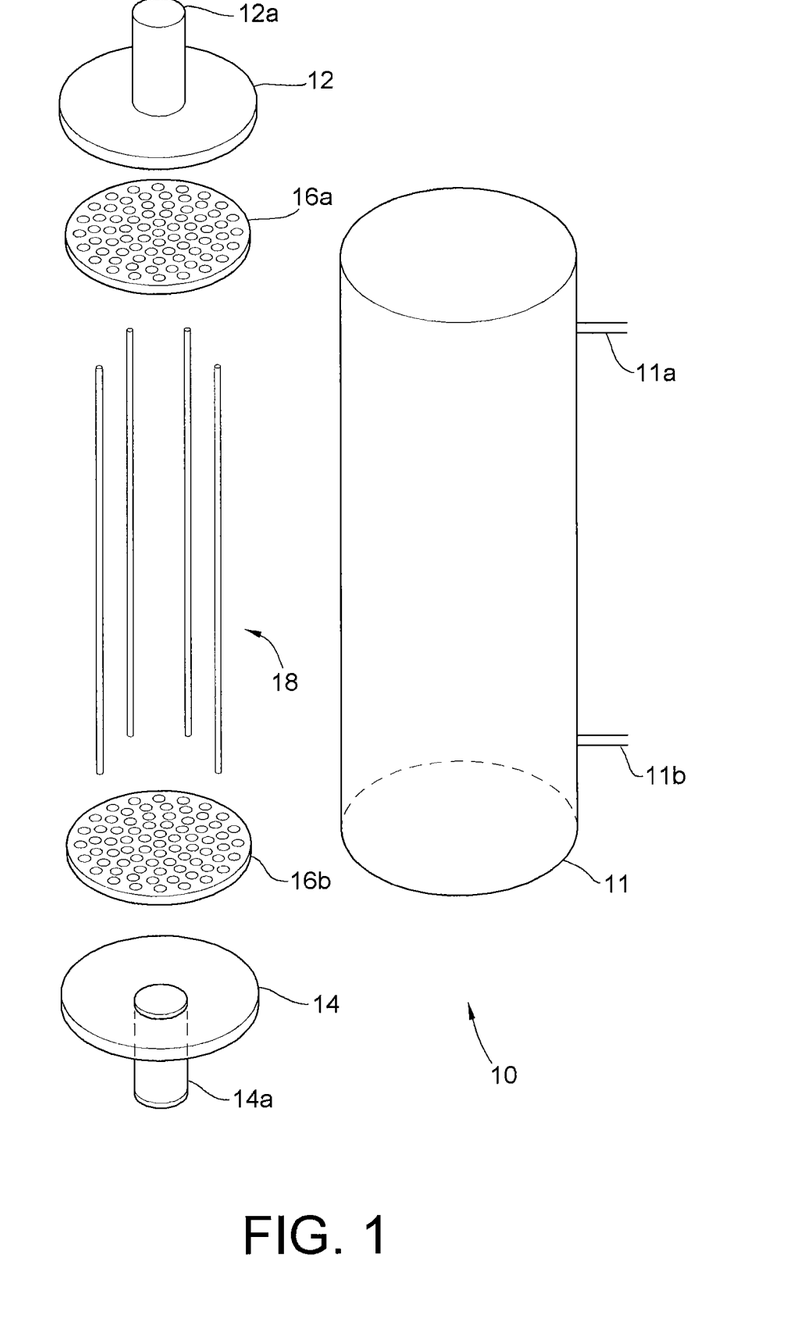
FIG. 1 is an exploded view of a dialyzer with porous multizone membranes.
Figure 2:
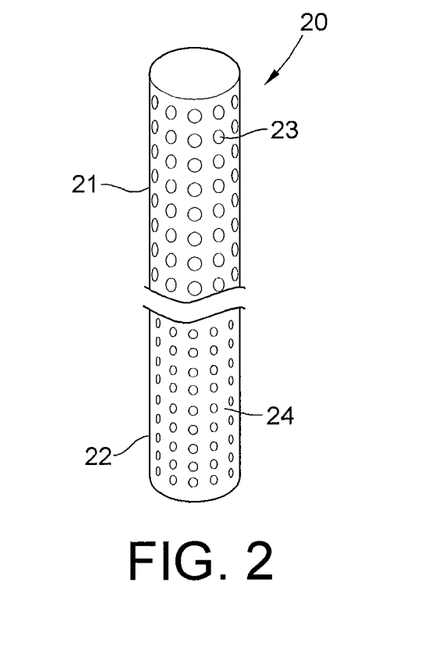
FIGS. 2-3 are closer views of porous multizone membrane embodiments.

An embodiment of a membrane formed by such a process, and a dialyzer using such membranes, is depicted in FIGS. 1-2. Dialyzer 10 includes a housing 11, with dialysate inlet and outlet ports 11b, 11a. The inlet cap 12 includes an inlet port 12a and the outlet cap 14 includes an outlet port 14a. The dialyzer includes a plurality of membranes 18 which are sealed to tubesheets 16a, 16b on both ends of the membranes. Blood enters and leaves the dialyzer through the end caps and ports and flows on the inside of the membranes. As shown in FIG. 2, each membrane 20 has an upper portion 21 and a lower portion 22. In the embodiment of FIG. 2, the pores 23 of the upper portion have larger diameters or openings, and the pores 24 of the lower portion have smaller diameters or openings. In one embodiment, pores 23 have an average MWCO of 50,000 Daltons, while pores 24 have an average MWCO of about 10,000 Daltons.

It will be recognized that pores formed in membranes do not generally enjoy a narrow distribution of sizes or diameters. Thus, any one size will necessarily encompass a range of sizes or diameters. When speaking of a portion with a particular size, it is understood that any such size is actually an average of what may be a wide distribution of sizes. When speaking of differences, such as different sizes of pores of different portions of a membrane, it is understood that an average or other measure is intended.

Figure 3:
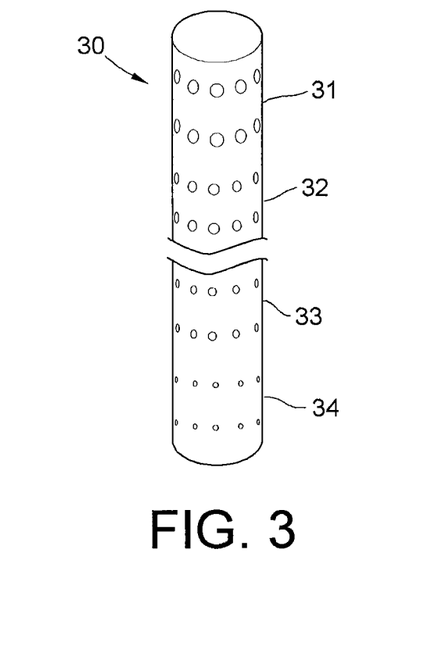

The zones of pores with different sizes are arranged along a longitudinal axis of the membranes. In hollow fiber membranes, as shown in FIGS. 1-3, one portion or end of the membrane may have pores with a smaller or larger size. For example, in a 10 cm hollow fiber, the top 5 cm may have pores with a larger size. In flat membranes that have a square or rectangular shape, such as those used in spiral-wound membranes, one portion of the membrane, defined along a width or length of the membrane, has pores with a smaller or larger size. For example, the bottom 5 cm of a rectangular membrane that is 15 cm long and 5 cm wide may have pores with a larger size, across the width of the membrane. The longitudinal spacing of the area or portion with a different pore size makes it convenient to process the fibers, membranes, or bundles of fibers or membranes. Processing can take place by immersing the longitudinally-spaced portion into a hot bath, into heated air, or into a coating, as will be described below. It is also possible to arrange for radial spacing of zones of different pores, such as an annular distribution, an inner circular portion with pores of one size and an outer portion with pores of a different size. Another possible radial distribution would be to have arcuate zones or portions, e.g., a 45° arc, or piece-of-pie-shaped zone, in a round or elliptical-shaped membrane.

It is also possible to make fibers with more than two zones. For instance, the membranes in the embodiment of FIGS. 1-2, may be made with a single immersion of the lower zone in a water bath of high temperature. It is also possible to vary the immersion depth and the immersion temperature, or both, so make multiple zones in a membrane. For example, the membrane 30 in FIG. 3 has been made by immersion in a cold bath, followed by immersion in a warmer bath for zones 32, 33, and 34, in which zone 31, at the top of the membrane was not immersed. After a period of time, typically a few minutes, the membrane or membranes are further withdrawn so that zones 31 and 32 are no longer immersed, and the temperature of the bath raised, thus encouraging further consolidation of zones 33 and 34. After another period of time, the membrane is further withdrawn, so that zone 33 is no longer immersed, only zone 34, and the temperature further raised. This graduated withdrawal results in a graduated series or range of pore sizes, from the largest at one end to the smallest at the opposite end.

The same result may be achieved by sequential immersion, rather than withdrawal, into baths of gradually decreasing temperature. Thus, membrane 30 may be made by first immersing the membrane, only to a depth that includes zone 34, into a bath at the highest temperature contemplated, such as 94° C., if membrane 30 is a cellulose acetate fiber. After a few minutes at this temperature, the membrane is withdrawn and then immersed in a second bath of lower temperature, such as 75° C., to a depth that includes zones 33 and 34. Since zone 34 was already subjected to a higher temperature, there is no further consolidation of the pores in the lower temperature used for both zones 33 and 34. The pores in zone 33 now consolidate, but because the temperature is less than that used for zone 34, the consolidation does not reduce the pore size to that of the pores in zone 34. The process is then repeated for zone 32, immersing zones 32, 33 and 34 in a bath with a yet-lower temperature than that used for zones 33 and 34. The pores of zone 31 may also be consolidated in a final bath, or they may be left unconsolidated.

In general terms, the liquid used to tighten the membrane and reduce the pore size and the MWCO is a liquid that plasticizes the polymer when warm or hot. Thus, water is a suitable heat-transfer medium for cellulosic membranes, but of course is limited to 100° C. at atmospheric pressures. Polyethylene glycol and glycerine, or mixtures of these with water, would also be suitable for heat-treating of cellulosic membranes. Polyacrylonitrile (PAN) fibers may be treated at least with aqueous dimethyl sulfoxide (DMSO). Polypropylene fibers or other olefin-type membranes may be treated with mineral oil. PVDF fibers may be treated with aqueous dimethylformamide or other suitable material. Other fibers include acrylics, acrylic copolymers, polycarbonate, polyurethanes, PTFE-type polymers, and suitable, compatible mixtures of any of these.

PVP is useful for treating PES or other polysulfone-based polymers. As noted above in the paper on PES/PVP membranes, the heat treatment may also take place by subjecting the membranes to a higher temperature in which heat transfer takes place via air or other gaseous medium. A liquid bath is easier to control, but air curtains can segregate portions of the membranes. Alternatively, sequential treatment of a first portion to the highest temperature contemplated, followed by treatment of larger portions to intermediate temperatures, will work well.

Figure 4:
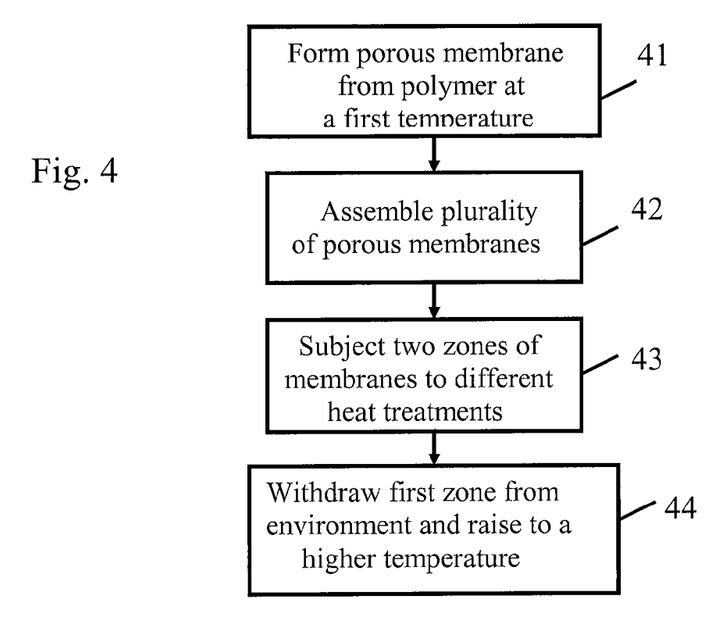
FIGS. 4-5 are flowcharts for two processes of making porous membranes.
Figure 5:
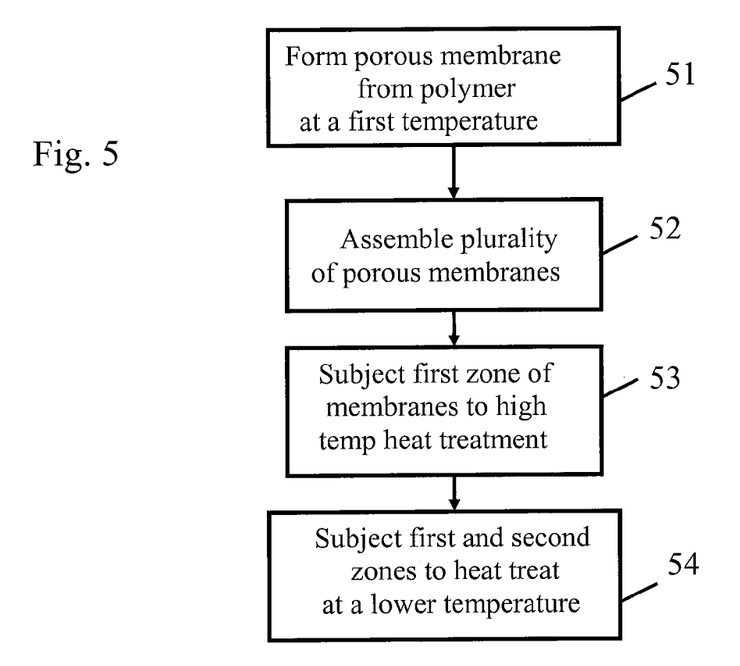

FIGS. 4 and 5 are flowcharts depicting processes such as these. FIG. 4 depicts a process in which most of the membrane is first immersed in a liquid bath or immersed in an air environment, followed by one or more stages of withdrawal. Alternatively, multiple baths, or air chambers, of sequentially higher temperature may be used in which less and less of the membranes are immersed or treated. In FIG. 4, porous polymer membranes are formed by first immersing or treating the entire membrane, or two or more portions, for treatment. In a first step 41 of the method, the porous membranes are formed from a polymer at a temperature. This temperature is typically that of ice water, or about 0° C. The membranes are then cut to length and assembled 42 into a plurality of membranes, which may be a bundle of membranes. The plurality of membranes or bundle are then heat-treated 43 by immersion into a liquid, such as water or other heat-transferring liquid. Alternatively, they are heat-treated by exposure to air or other gaseous heat transfer medium at that temperature. In this process, this first step of heat-treating takes place at a lower temperature than the subsequent step 44, which will be at a higher temperature. Thus, the first treating step accommodates at least two zones or lengths of the membranes, of which one zone is withdrawn before the temperature is raised. If multiple baths are used, the membranes are not immersed as deeply into the second or subsequent bath, which is at a higher temperature. The same follows for air treatment, but air or other gaseous medium can typically be heated more quickly than a bath of liquid. The process continues for as many zones as are desired.

FIG. 5 depicts a process similar to that of FIG. 4 in which only a portion of the membranes is first immersed into the bath at the warmest temperature contemplated, followed by further immersion into baths of sequentially lower temperatures. This technique may also be applied for air treatment, with only a portion of the membranes being exposed to the first, highest temperature of the medium. In FIG. 5, the first step 51 is to form the porous membranes at a first temperature. The membranes are then cut to length and assembled 52 into a plurality of membranes for further processing. One or more zones of the membranes are then heat treated by being immersed into a heat-transfer liquid, such as water, or other solvent in which the polymer of which the membrane is comprised and which solvent does not dissolve the polymer (or polymer blend). This liquid is at the highest temperature contemplated for treatment for the membranes. After a short period of time, the temperature is lowered or the membranes are removed and then immersed 54 into a second bath at a temperature lower than the highest temperature. The membranes are further immersed, the immersion including the zone of immersion of the first zone and a second zone. Because the second bath is at a lower temperature than the first bath, which is at the highest temperature, no further consolidation takes place for the first zone at the lower temperature. The second zone, however, has not been subjected to this high temperature, and thus it will consolidate, but not to the extent that took place with the zone subjected to the highest temperature. The process may continue for as many zones as desired. Rather than baths of liquid, purified, filtered air or other gaseous medium, such as nitrogen, may be used instead.

These processes have the advantage of separating steps that determine the final pore size from the steps that make the membrane and the initial pore size. That is, the manufacturer now has a greater degree of freedom in determining the pore size, and the variations in pore size, for the membranes manufactured by virtually any of the above-described processes.

Processing different portions of membranes at different temperatures is not the only way to produce a membrane having multiple zones of pore sizes. There are also processes, which may be loosely termed coating processes, that can be used on different zones or areas of a membrane to produce zones with different pore sizes. For example, a portion of a length of a formed membrane may be coated with one substance and then reacted with a second substance to form a thin coating on the membrane. The coating acts partially to close up the pores in the membrane, and thus lowers the pore size in the areas which are coated. In other techniques, an already formed hydrophobic membrane receives a hydrophilic coating to modify pore sizes. There are several techniques that may be used. In general terms, a membrane, or a portion of a membrane, is coated with one or more substances, which are then dried or reacted chemically with another substance to alter the diameter or size of the pores in that portion of the membrane. The coating may also be applied by spraying.

In one technique, described in U.S. Pat. No. 4,039,440, which is hereby incorporated by reference in its entirety, a formed membrane with pores is coated with a first polymer, and then cross-linked to complete the reaction and limit the pore sizes to a size smaller than the as-formed pore size. For example, a PES or chlorinated polyvinylchloride membrane is immersed in a solution of polyethylene-imine (PEI), a highly branched amine. The membrane is then allowed to dry and is immersed in a solution of a suitable cross-linking agent, such as toluenediisocyante (TDI) or isophthaloyl chloride (IPC). Other suitable curing or cross-linking agents may also be used, such as terephthaloyl chloride, disulfonyl chloride, cyanuric chloride (2,4,6-trichloro-s-triazine), and diphenyldisulfonyl chloride. In general terms, the cross-linking agents are heterocyclic or aromatic, and are polyfunctional, with acid chloride or isocyanate functional groups.

The membranes are then dried at room temperature or at an elevated temperature. The amount of "closing-up" of the pores can be adjusted by selection of the concentration of the PEI, the selection and concentration of the cross-linking agent, the temperature of immersion of the membrane in the cross-linking agent, and the temperature and duration of the final drying step, which may range from room temperature to 130° C. or higher, for periods from 5 to 30 minutes. Other times and temperatures may be used. Suitable concentration of the PEI range from about 0.3% in water to about 2% in water. Immersion of the membrane in PEI may be accomplished with a contact time of about 1 minute. Cross-linking agent concentrations may be from about 0.1% to about 2% in an aprotic solvent, such as an alkane, of which n-heptane is an example. By treating only a portion of a length of a hollow fiber membrane by these techniques, a similar effect is obtained and membranes with multiple zones of pore sizes may be obtained. Membranes, or portions of membranes treated with such coatings, have significant reductions in pore size, as was shown with tests for desalinization of water.

Other coating techniques are revealed in U.S. Pat. No. 4,824,568, which is hereby incorporated by reference in its entirety, in which polyvinylidenefluoride (PVDF) membranes receive an ultrafiltration membrane coating, which is actually precipitated from a solution that is applied to the membrane. In this technique, an already-formed membrane is coated with a liquid protecting agent. The protective agent is believed to help protect the surface of the membrane from attack by the polymer solvent used later in the process and to prevent penetration of the membrane by the solvent. One example is a membrane made from PVDF coated with another film made from PVDF. The membrane is coated with a protecting agent, i.e., a polymer dissolved in a solvent. One example is a solution of about 15-40% glycerine dissolved in isopropyl alcohol (IPA). Other protecting agents include ethylene glycol, propylene glycol, triethylene glycol, and the like, dissolved in water. Water-soluble waxes, such as polyethylene oxides, may also be used. Water is the preferred solvent, since it is low in cost and easily removed.

The membrane to be treated is coated with the solution of protective agent. The solvent is evaporated or dried, and the membrane is then treated with a solution of an ultrafiltration membrane. An example is a 10% PVDF solution in dimethylacetamide, with 3% lithium chloride as a precipitating agent. Immersion time is short, about 1 second. The coated membrane is then immersed in a water bath or a bath of other solvent, in which the solvent is miscible but is not a solvent for the membrane. Contact time of about one minute is sufficient, after which the coated membrane is dried. The temperature of drying helps to determine the final pore size and may be accomplished at temperatures that achieve the desired pore size or porosity, e.g., 130° C. or other suitable temperature. Heated air may be used.

This technique may be used on other combinations besides a PVDF coating on a PVDF membrane, and may be combined with the temperature and zone techniques described above. Other combinations of membrane and coating include polyethylene terephthalate (PET)/PVDF, PVDF/Kynar 741 and PVDF/PES. Kynar is a brand of PVDF from Arkema, Inc., Philadelphia, Pa., U.S.A. In these examples, the PVDF solutions comprised 20% Kynar 741, 3% LiCl, and the balance dimethylacetamide solvent, and 18% PES (Victrex from ICI), 5% LiCl, and the balance N-methyl-pyrrolidone (NMP) solvent. Other solutions suitable for this technique are described in U.S. Pat. No. 7,208,200, which is hereby incorporated by reference in its entirety. These include PVDF in NMP, cellulose diacetate in acetone and methyl-2,4-pentanediol (MPD), and PES in NMP and triethylene glycol. The polymer is typically present from about 9-20%. Other concentrations may be used. The techniques described above for creating zones in hollow fiber membranes with different pore sizes may be used in combination with this application technique to create membranes for dialysis or other purposes that have two or more zones with pores of different sizes.

Similar techniques for varying pore size are also described in U.S. Pat. No. 5,017,292, and U.S. Pat. No. 5,228,994, which are hereby incorporated by reference in their entirety. In the first of these, a coating solution is prepared from about 20.5% PVDF and 4.9% LiCl, in NMP, and was applied to a PVDF membrane. After the application, the coated membrane was immersed in a bath of water with 25 wt % glycerine at 7° C. for a very brief moment, immersed in a water bath at 25° C. for 1 minute, and then dried in a 140° C. air stream. Other variations on this technique are also reported, all of which are incorporated herein by reference, as though each were set forth herein, word for word.

Once the membranes with portions having pores of different sizes have been made, a dialyzer or other separator may be assembled using the membranes. A process for accomplishing dialysis is disclosed in FIG. 6. In a first step of the process, a user provides 61 a dialyzer with a housing and a tube bundle made from porous membranes, each membrane having two zones, one zone with pores having a larger dimension or size, and the other zone with pores having a smaller dimension or size. The dialyzer is used in a hemodialysis machine, which pumps 62 blood into the dialyzer using the dialyzer blood inlet port that is nearer the membrane zone with the larger pores. The hemodialysis machine also pumps 63 dialysate into the dialyzer on an opposite side from the permeable membranes using the dialysis inlet port.

Figure 6:
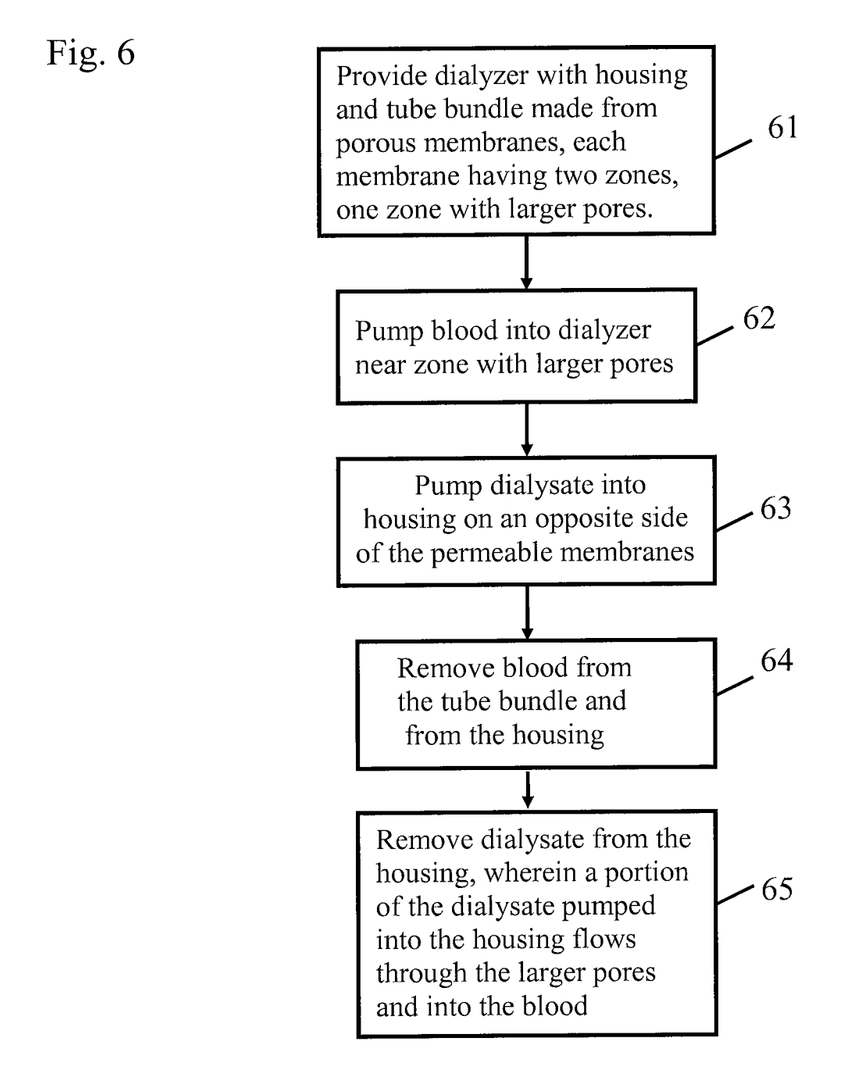
FIG. 6 is a flowchart depicting a method for using multi-zone membranes for hemodialysis.

The dialyzer flows the blood and the dialysate in a counter-current manner, so that clean dialysate from the inlet flows in the direction opposite that of the blood. At the end of the dialysis treatment, the remaining blood is returned 64 to the patient, and the dialysate fluid is removed 65 from the dialyzer and the dialyzer housing.

During a dialysis procedure, the blood is typically always at a higher pressure than the dialysate. In counter-current flow, the blood entering the dialyzer is at its highest pressure and is on the inside of the membranes. The dialysate, on the outside of the membranes, is at its lowest pressure as it leaves the dialyzer at a point near the blood inlet. With larger pores, the dialysate fluid, typically including water with glucose or other osmotic agent, can flow through the larger pores to a small extent, across the membrane, and into the blood. This is a form of diafiltration, in which dialysis fluid is introduced into the blood for the purpose of enhancing dialysis. The extra fluid dilutes the blood and allows the toxins in the blood to flow into the dialysate and water that has crossed the membrane and has been added to the blood.

Along the length of the membrane, the pore size lowers and it is more difficult for the dialysate to cross into blood. Nevertheless, the blood remains at a higher pressure than the dialysate, and hemodialysis continues to occur, as the lower molecular-weight substances diffuse through and convect across the membranes. The process is enhanced by the small volume of dialysis fluid that has crossed the membrane, and has lowered the viscosity and surface tension of the blood. In a counter-current environment, the dialysate entering is at its highest pressure, while the blood leaving is at its lowest pressure but still higher than that of the dialysate at any point along the dialyzer. Membranes made by this process, and membrane embodiments, may also be used in co-current applications, with blood and dialysate entering the same end of the dialyzer, and both leaving from the opposite end. The pumps can be controlled to provide roughly an equal pressure drop along the entire length of the dialyzer, the blood pressure higher than the dialysate pressure by a constant amount, or the pressure drop could otherwise be tailored as desired for co-current flow.

In addition to the hollow membrane fibers that are typically preferred for dialysis applications, flat membrane sheets prepared by any of the techniques described above may also be prepared. These flat sheets find use in many types of separators, such as plate and frame type exchangers in which impermeable feed layers alternate with permeable or semi-permeable membranes to effect separation. Another example is a spiral-wound separation module, such as those depicted in U.S. Pat. No. 5,538,642, which is hereby incorporated by reference in its entirety.

Figure 7:
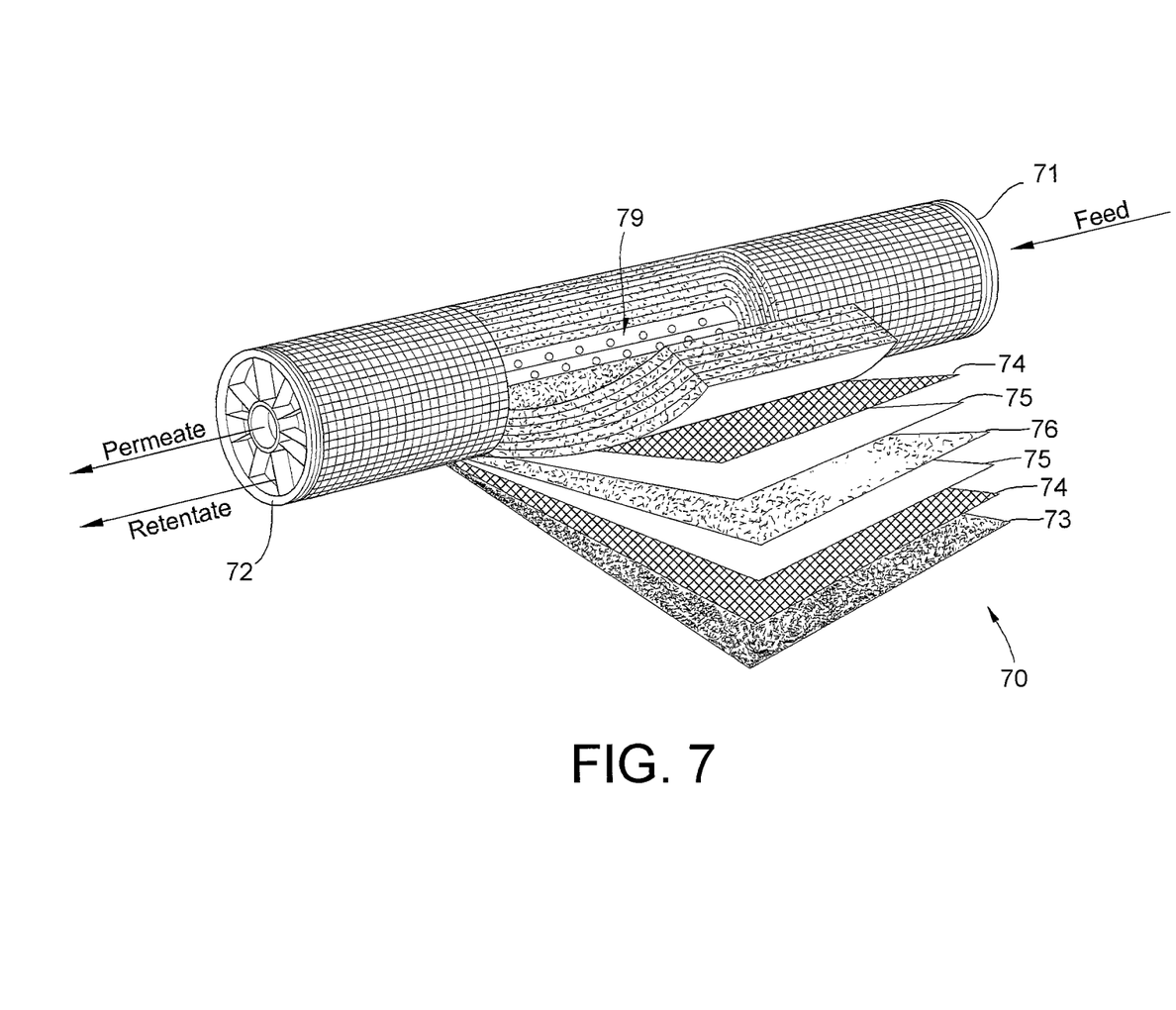
FIG. 7 is a perspective view of a radial-wound separation-processing device.

A typical spiral-wound separator, as used for many separation processes, is depicted in FIG. 7. Spiral-wound separator 70 includes a first end plate 71 a central perforated feed tube, a second end plate 72, and an outer cover 73. Feed enters through first end plate 71 and is routed to the perforated central tube 79. The feed then is routed between one or more impermeable layers 76 where it contacts a separation membrane 75. The layers may be separated by channel spacers 74. The portion that can pass through the membrane, such as filtrate, ultrafiltrate or permeate, passes through and is routed to the permeate outlet as shown. The remainder, the concentrate or retentate, remains on the first side of the separation membrane, and is routed to the retentate outlet as shown. Membranes for spiral separators, with a first zone having pores of a first size, and a second zone having pores of a second, different size, may be made by any of the above techniques.

The membranes and the processing techniques discussed above have been developed primarily for dialysis, in particular for hemodialysis. However, these membranes may also be used for general separations of other types, such as filtering water or other solvents, food processing, chemical separation processes, plating bath purification, and so forth. As discussed above, the words permeable and semi-permeable are used interchangeably for membranes whose permeability characteristics are tailored according to embodiments of the present invention.

It is understood that various changes and modifications to the presently preferred embodiments described herein will be apparent to those skilled in the art. Such changes and modifications can be made without departing from the spirit and scope of the present subject matter and without diminishing its intended advantages. It is intended that such changes and modifications be covered by the appended claims.

What is claimed is:

1. A method for making a permeable membrane, the method comprising:
    forming a membrane, the membrane comprising a polymer continuum with a first plurality of pores, the first plurality of pores having an average molecular weight cut-off of about 50,000 Daltons; and
    immersing a first longitudinally-spaced portion of the formed membrane that is less than the entire longitudinal length of the membrane in a first temperature environment, wherein the first temperature is higher than a temperature of formation of the membrane and causes the first portion of the membrane to consolidate and form a second plurality of pores in the first portion of the membrane subjected to the first temperature environment, a size of the second plurality of pores being smaller than a size of the first plurality of pores.

2. The method of claim 1, wherein the first temperature environment is selected from the group consisting of a liquid environment and an air environment.

3. The method of claim 1, wherein the first longitudinally-spaced portion is immersed in a bath heated to 60° C.

4. The method of claim 1, further comprising:
    exposing a second longitudinally-spaced portion of the membrane to a second temperature, the second longitudinally-spaced portion of the membrane less than the entire longitudinal length of the membrane and less than or equal to the first longitudinally-spaced portion, the second temperature higher than the first temperature, wherein the membrane forms a third plurality of pores in the second longitudinally-spaced portion of the membrane heated to the second temperature, a size of the pores of the third plurality being smaller than a size of the pores of the second plurality.

5. The method of claim 4, wherein the step of exposing the second longitudinally-spaced portion of the membrane to the second temperature is accomplished by removing the membrane from the first environment and immersing the second longitudinally-spaced portion of the membrane, the second longitudinally-spaced portion different from the entire first longitudinally-spaced portion, into the second environment at the second temperature, resulting in a range of pore sizes from the pore size formed at the first temperature to a pore size formed at the second temperature.

6. The method of claim 1, wherein the first temperature environment is a temperature-controlled liquid bath or a gaseous atmosphere, at a temperature higher than a temperature of formation of the membrane.

7. The method of claim 1, wherein the permeable membrane has a shape of a narrow hollow fiber, and further comprising:
    assembling a plurality of the permeable membranes in the shape of the narrow hollow fiber into a bundle; and
    assembling the bundle into a housing to form a dialyzer.

8. The method of claim 1, wherein the permeable membrane has a shape of a sheet.

9. A method of making a permeable polymer membrane for hemodialysis, the method comprising:
    forming a polymer membrane for hemodialysis, the polymer membrane comprising a first plurality of pores, the first plurality of pores having an average molecular weight cut-off of about 50,000 Daltons;
    subjecting a first longitudinal portion of the formed polymer membrane, the first longitudinal portion less than the entire longitudinal length of the polymer membrane, to an environment at a first temperature, wherein the first temperature is higher than a temperature of formation of the membrane and causes the first longitudinal portion of the membrane to consolidate and form a second plurality of pores in the first longitudinal portion at the first temperature, a size of the pores of the second plurality being smaller than a size of the pores of the first plurality.

10. The method of claim 9, further comprising subjecting a second longitudinal portion of the polymer membrane, the second longitudinal portion less than the entire membrane and less than the first longitudinal portion, to a second environment at a second temperature, the second temperature between the first temperature and the temperature of formation of the membrane, wherein the membrane forms a third plurality of pores in the second longitudinal portion at the second temperature, a size of the pores of the third plurality being larger than the size of the pores of the second plurality.

11. The method of claim 10, wherein the step of subjecting the second longitudinal portion of the membrane to the environment at the second temperature is accomplished by further immersing the membrane into the first environment while the first environment is cooled to the second temperature to form the second environment, resulting in a range of pore sizes from the pore size formed at the first temperature to the pore size formed at the second temperature.

12. The method of claim 9, wherein the permeable membrane for hemodialysis has a shape of a hollow fiber, and further comprising:
   assembling a plurality of permeable membranes into a bundle; and
   assembling the bundle into a housing to form a dialyzer.

13. The method of claim 9, further comprising:
   assembling a plurality of the permeable membranes for hemodialysis in the shape of a tube into a tube bundle;
   assembling the bundle into a housing to form a dialyzer;
   pumping blood into the housing and into the tube bundle;
   pumping dialysate into the housing on an outside of the tube bundle, wherein a portion of the dialysate crosses the membranes and enters the blood;
   removing blood from the tube bundle and the housing; and
   removing dialysate from the housing.

14. The method of claim 13, wherein in the step of pumping blood, the blood flows into an end of the tube bundle having pores from the first plurality of pores, and wherein in the step of removing blood, the blood flows from an end of the tube bundle having pores from the second plurality of pores.

15. The method of claim 9, wherein the membrane comprises a polymer of polyethersulfone, polyarylethersulfone, olefin, cellulose, cellulose acetate, cellulose acetate-butyrate, cellulose propionate, ethyl cellulose, cellulose derivative, or PVDF.

16. A method of making a permeable membrane, the method comprising:
   forming a polymer membrane, the polymer membrane comprising a first plurality of pores, the first plurality of pores having an average molecular weight cut-off of about 50,000 Daltons;
   immersing a first longitudinal portion of the membrane that is less than the entire longitudinal length of the membrane in a first temperature environment, wherein the first temperature is higher than a temperature of formation of the membrane and causes the first portion of the membrane to consolidate and forms a second plurality of pores in the portion of the membrane subjected to the first temperature environment, the second plurality of pores having an average molecular weight cut-off of about 10,000 Daltons; and
   coating a portion of the polymer membrane, the coated portion less than the entire membrane, wherein the coating reduces the size of the pores in the coated portion.

17. The method of claim 16, wherein the coating is applied by dipping or spraying a polymer coating on the polymer membrane.

* * * * *